(12) United States Patent
Carter et al.

(10) Patent No.: US 11,021,700 B2
(45) Date of Patent: Jun. 1, 2021

(54) METHOD FOR PURIFYING VIRAL VECTORS

(71) Applicant: SARTORIUS LAB INSTRUMENTS GMBH & CO. KG, Gottingen (DE)

(72) Inventors: Paul Stephen Carter, Stevenage (GB); Sara Margareta Nilsson, Stevenage (GB)

(73) Assignee: SARTORIUS LAB INSTRUMENTS GMBH & CO. KG, Gottingen (DE)

( * ) Notice: Subject to any disclaimer, the term of this patent is extended or adjusted under 35 U.S.C. 154(b) by 327 days.

(21) Appl. No.: 15/677,175

(22) Filed: Aug. 15, 2017

(65) Prior Publication Data
US 2018/0051275 A1 Feb. 22, 2018

(51) Int. Cl.
| | | |
|---|---|---|
| *C12N 15/10* | (2006.01) | |
| *C12N 15/86* | (2006.01) | |
| *A61K 48/00* | (2006.01) | |
| *C12N 7/00* | (2006.01) | |
| *C12N 7/02* | (2006.01) | |

(52) U.S. Cl.
CPC ...... *C12N 15/1017* (2013.01); *A61K 48/0091* (2013.01); *C12N 7/00* (2013.01); *C12N 15/86* (2013.01); *C12N 2740/15043* (2013.01); *C12N 2740/15051* (2013.01)

(58) Field of Classification Search
CPC ...... C12N 15/1017; C12N 15/86; C12N 7/00; C12N 7/02; C12N 2740/15051; C12N 2740/15043; A61K 48/0091
See application file for complete search history.

(56) References Cited

U.S. PATENT DOCUMENTS

| | | | | |
|---|---|---|---|---|
| 5,576,196 A | * | 11/1996 | Horn | C12N 1/08 435/5 |
| 2001/0043916 A1 | * | 11/2001 | McNeilly | C12N 7/00 424/93.6 |
| 2009/0275107 A1 | * | 11/2009 | Lock | C12N 7/00 435/239 |
| 2009/0325284 A1 | * | 12/2009 | Truran | A61K 48/0091 435/320.1 |

FOREIGN PATENT DOCUMENTS

| | | |
|---|---|---|
| WO | WO 01/48155 A2 | 7/2001 |
| WO | WO2009/082664 A2 | 7/2009 |
| WO | WO2009/153563 A1 | 12/2009 |
| WO | WO2012/069190 A2 | 5/2012 |
| WO | WO 2013/192604 | 12/2013 |

OTHER PUBLICATIONS

PCT/EP2017/070668 WOISA (Year: 2018).*
Van der Meer T, Minow B, Lagrange B, Krumbein F, Rolin F. Sep. 2014 Diatomaceous Earth Filtration: Innovative Single-Use Concepts for Clarification of High-Density Mammalian Cell Cultures. BioProcess International (September). (Year: 2014).*
Lise, et al., *Biotechnology Advances*, Clarification of vaccines: An overview of filter based technology trends and best practices, 34(1):1-13 (2015).
Nestola, et al., *Biotechnology and Bioengineering*, Improved virus purification processes for vaccines and gene therapy, 112(5):843-857 (2015).
Thomassen, et al., *Biotechnol. Bioeng.*, Article Scale-Down of the Inactivated Polio Vaccine Production Process, 1354-1365 (2013).

* cited by examiner

*Primary Examiner* — Liam Royce
(74) *Attorney, Agent, or Firm* — Stinson LLP

(57) ABSTRACT

The invention relates to methods of purifying viral vectors from cell culture. In particular, the invention relates to a method of purifying a supernatant containing viral vectors from a cell culture by removing cells by filtering the cell culture using diatomaceous earth.

13 Claims, No Drawings

METHOD FOR PURIFYING VIRAL VECTORS

CROSS REFERENCE TO RELATED APPLICATION

This application claims the benefit of U.K. Provisional Application No. GB 1614050.1, filed 17 Aug. 2016.

FIELD OF THE INVENTION

The present invention relates generally to the field of purifying viral vectors, in particular viral vectors for use in methods of gene therapy.

BACKGROUND TO THE INVENTION

In gene therapy, genetic material is delivered to endogenous cells in a subject in need of treatment. The genetic material may introduce novel genes to the subject, or introduce additional copies of pre-existing genes, or introduce different alleles or variants of genes that are present in the subject. Viral vector systems have been proposed as an effective gene delivery method for use in gene therapy (Verma and Somia (1997) Nature 389: 239-242).

One of the many challenges associated with gene therapies, is the need for fast, simple and inexpensive downstream processing to purify the viral vectors used to transfer genetic material into patients. In particular, effective removal of host cell proteins and DNA is critical in the purification of viral vectors, especially for viral vectors intended for clinical use.

Many primary recovery (cell removal) steps that could be used when purifying viral vectors for gene therapy have been shown to be unsuitable, for a number of different reasons. Centrifugation at large scale using disk stack centrifugation, lyses the cells on discharge due to the pressure drop when removing the cells from the centrifuge, adding additional host cell proteins that need to be removed during the downstream processing. Depth filters, that are successfully used in the purification of monoclonal antibodies, contain materials that have a strong positive charge on them; this positive charge irreversibly binds the negatively charged viral vectors, making them unsuitable filters. Tangential flow micro filtration using either hollow fibres or membrane stacks, is not suitable for the primary recovery step when working with viral vectors, because the pumping of the process fluid around the system generates shear. Viral vectors are sensitive to the shear which disrupts the viral particles leading to significant decreases in infectivity.

WO01/48155 describes the use of diatomaceous earth to purify viruses obtained from cell lysate. This disclosure requires a step of cell lysis which creates a culture containing significant amounts of contaminating cellular debris, such as host cell DNA and protein.

It is therefore an object of the present invention to provide improved methods of purifying viral vector from cell culture, in particular purifying suspension cultures expressing lentiviral vectors.

SUMMARY OF THE INVENTION

There are several filters currently available which can be used to purify viral vectors from cell culture, however the concentration of unwanted host cell proteins and DNA is often too high and can end up blocking the filter. For example, 0.45 μm membrane filters are particularly useful in the purification of viruses, however the small pore size in the filter can quickly become clogged if cell culture is added to it directly.

The present inventors have found that the use of diatomaceous earth to initially purify the cell culture can significantly improve the overall purification process. Diatomaceous earth is highly porous and is less likely to become blocked when filtering cell culture.

Therefore, according to a first aspect of the invention, there is provided a method of purifying a supernatant containing viral vectors from a cell culture, comprising removing cells by filtering the cell culture using diatomaceous earth (DE).

Furthermore, the present inventors have found that there is an optimum amount of diatomaceous earth to use when purifying viral vectors. Interestingly, using the recommended maximum amount of diatomaceous earth caused a decrease in percentage recovery of viral vector. Reducing the amount of diatomaceous earth has the added advantage of reducing the cost of goods when purifying viral vectors.

Therefore, according to a further aspect of the invention, there is provided a method of purifying a supernatant containing viral vectors from a cell culture, comprising the steps of:

(i) calculating the percentage of wet cell weight in the cell culture;

(ii) calculating the amount of diatomaceous earth to use when purifying the supernatant containing viral vectors from the cell culture so that the amount of diatomaceous earth is 2-4 g DE/litre/% of wet cell weight; and (iii) removing cells by filtering said cell culture using the amount of diatomaceous earth calculated in step (ii).

DETAILED DESCRIPTION OF THE INVENTION

Definitions

Unless defined otherwise, all technical and scientific terms used herein have the same meaning as is commonly understood by one of skill in the art (e.g., in cell culture, molecular genetics, nucleic acid chemistry, hybridization techniques and biochemistry). Standard techniques are used for molecular, genetic and biochemical methods (see generally, Sambrook et al., Molecular Cloning: A Laboratory Manual, $2^{nd}$ ed. (1989) Cold Spring Harbor Laboratory Press, Cold Spring Harbor, N.Y. and Ausubel et al., Short Protocols in Molecular Biology (1999) $4^{th}$ Ed, John Wiley & Sons, Inc. which are incorporated herein by reference in their entirety) and chemical methods. All patents and publications referred to herein are incorporated by reference in their entirety.

The term "comprising" encompasses "including" or "consisting" e.g. a composition "comprising" X may consist exclusively of X or may include something additional e.g. X+Y.

The term "consisting essentially of" limits the scope of the feature to the specified materials or steps and those that do not materially affect the basic characteristic(s) of the claimed feature.

The term "consisting of" excludes the presence of any additional component(s).

The term "about" as used herein when referring to a measurable value such as an amount, a temporal duration, and the like, is meant to encompass variations of ±20% or ±10%, including ±5%, ±1%, and ±0.1% from the specified value.

The term "vector" refers to a vehicle which is able to artificially carry foreign genetic material into another cell, where it can be replicated and/or expressed. Examples of vectors include plasmids and viral vectors, such as retroviral and lentiviral vectors, which are of particular interest in the present application. Lentiviral vectors, such as those based upon Human Immunodeficiency Virus Type 1 (HIV-1) are widely used as they are able to integrate into non-proliferating cells. Viral vectors can be made replication defective by splitting the viral genome into separate parts, e.g., by placing on separate plasmids. For example, the so-called first generation of lentiviral vectors, developed by the Salk Institute for Biological Studies, was built as a three-plasmid expression system consisting of a packaging expression cassette, the envelope expression cassette and the vector expression cassette. The "packaging plasmid" contains the entire gag-pol sequences, the regulatory (tat and rev) and the accessory (vif, vpr, vpu, nef) sequences. The "envelope plasmid" holds the Vesicular Stomatitis Virus glycoprotein (VSVg) in substitution for the native HIV-1 envelope protein, under the control of a cytomegalovirus (CMV) promoter. The third plasmid (the "transfer plasmid") carries the Long Terminal Repeats (LTRs), encapsulation sequence ($\psi$), the Rev Response Element (RRE) sequence and the CMV promoter to express the transgene inside the host cell.

The second lentiviral vector generation was characterized by the deletion of the virulence sequences vpr, vif, vpu and nef. The packaging vector was reduced to gag, pol, tat and rev genes, therefore increasing the safety of the system.

To improve the lentiviral system, the third-generation vectors have been designed by removing the tat gene from the packaging construct and inactivating the LTR from the vector cassette, therefore reducing problems related to insertional mutagenesis effects.

The various lentivirus generations are described in the following references: First generation: Naldini et al. (1996) *Science* 272(5259): 263-7; Second generation: Zufferey et al. (1997) *Nat. Biotechnol.* 15(9): 871-5; Third generation: Dull et al. (1998) *J. Virol.* 72(11): 8463-7, all of which are incorporated herein by reference in their entirety. A review on the development of lentiviral vectors can be found in Sakuma et al. (2012) *Biochem. J.* 443(3): 603-18 and Picanco-Castro et al. (2008) *Exp. Opin. Therap. Patents* 18(5):525-539.

It will be understood that references to "viral vector" as used herein, refer to viral particles which have been modified to carry genetic material into cells and not natural, unmodified viruses that occur in nature.

The terms "transfection", "transformation" and "transduction" as used herein, may be used to describe the insertion of the vector into the target cell. Insertion of a vector is usually called transformation for bacterial cells and transfection for eukaryotic cells, although insertion of a viral vector may also be called transduction.

The term "packaging cell line" refers to a cell line containing the viral genes required for packaging, e.g. the gag and pol protein and envelope glycoprotein genes for retroviral vectors. Alternatively, the term "producer cell line" refers to a packaging cell line which also contains the transfer vector (i.e. the viral vector genome) containing a transgene of interest.

The term "transgene" refers to heterologous or foreign DNA which is not present or not sufficiently expressed in the host cell in which it is introduced. This may include, for example, when a target gene is not expressed correctly in the host cell, therefore a corrected version of the target gene is introduced as the transgene. Therefore, the transgene may be a gene of potential therapeutic interest. The transgene may have been obtained from another cell type, or another species, or prepared synthetically. Alternatively, the transgene may have been obtained from the host cell, but operably linked to regulatory regions which are different to those present in the native gene. Alternatively, the transgene may be a different allele or variant of a gene present in the host cell.

References to "wet cell weight" or "wcw" as used herein refer to the weight of cells in culture when they are wet, i.e. immediately after they are removed from culture broth and not dried prior to weighing. For example, wet cell weights can be calculated by aliquoting samples of cell culture into pre weighed centrifuge tubes and centrifuging (e.g. for about 10 minutes at 1000 g at 4° C.). The supernatant can be recovered into another pre weighed centrifuge tube and the weights of both the pellet and the supernatant determined. These weights can be expressed in grams per litre and/or as a percentage.

Described herein is a method of purifying viral vectors from cell culture comprising filtering the cell culture using diatomaceous earth (DE). Therefore, according to a first aspect of the invention, there is provided a method of purifying a supernatant containing viral vectors from a cell culture, wherein the method comprises removing cells by filtering the cell culture using DE.

Diatomaceous earth, or diatomaceous silica, is a naturally occurring sedimentary rock that consists of fossilized remains of diatoms. DE has previously been used as a filter due to its high porosity.

The present invention uses DE to remove cells from the cell culture as a gentle method for purifying the cell culture supernatant which contains the viral vectors. This supernatant can then be passed through subsequent filter steps without the cells clogging up the filters. DE is therefore used as an initial filtration step.

In one embodiment, the method comprises:
(a) transfecting cells with genes encoding a viral vector;
(b) culturing the cells in order to produce the viral vector; and
(c) filtering the culture using DE in order to remove cells and collect the supernatant which contains the viral vectors.

In methods of the invention, the cells are not lysed prior to filtering the cell culture using DE. Instead, the viral vectors present in the supernatant are collected. Certain types of viral vectors, such as lentivirus, are sensitive to shear, therefore cell lysis and/or harsh conditions should be avoided in order to maintain viral vector titre and infectivity. Cell lysis is also not preferable in methods of viral vector production because smaller cell contaminants, such as host cell protein and DNA, are released into the cell culture and are more difficult to remove during viral vector purification.

Cell culturing may be conducted in a bioreactor, i.e. a device or system that supports a biologically active environment. Bioreactors are known in the art and include fed batch or continuous reactors, and reactors where cells are submerged in liquid medium (suspended or immobilized) or attached to the surface of a solid medium. In one embodiment, the DE is added directly to a bioreactor containing the cell culture. In this embodiment, at the end of cell culturing, the bioreactor is drained and the DE collects on a filter at the exit of the bioreactor thus acting as an initial filter to remove the cells and allow the supernatant containing the viral vectors to pass out and be collected. In a further embodiment, the bioreactor is a stirred-tank bioreactor. This therefore has the advantage that the DE is mixed with the cell culture by virtue of the stirrer.

The present inventors have also found that there is an optimum amount of diatomaceous earth to use when purifying viral vectors. Therefore, in one embodiment, the method additionally comprises:

(a) calculating the percentage of wet cell weight in the cell culture;

(b) calculating the amount of diatomaceous earth to use when purifying the supernatant containing viral vectors from the cell culture so that the amount of diatomaceous earth is 2-4 g DE/litre/% of wet cell weight.

According to a further aspect of the invention, there is provided a method of purifying a supernatant containing viral vectors from a cell culture, comprising the steps of:

(i) calculating the percentage of wet cell weight in the cell culture;

(ii) calculating the amount of diatomaceous earth to use when purifying the supernatant containing viral vectors from the cell culture so that the amount of diatomaceous earth is 2-4 g DE/litre/% of wet cell weight; and (iii) removing cells by filtering said cell culture using the amount of diatomaceous earth calculated in step (ii).

According to a further aspect of the invention, there is provided a method of determining the optimal amount of diatomaceous earth to use for purifying viral vectors from cell culture comprising:

(a) calculating the percentage (%) of wet cell weight in the cell culture;

(b) calculating the amount of diatomaceous earth to use when purifying the viral vectors from the cell culture so that the amount of diatomaceous earth is 2-4 g DE/litre/% of wet cell weight. This amount can then be added to a cell culture comprising a virus-containing supernatant in order to remove cells from the supernatant.

As shown in the data described herein, the inventors surprisingly found there is an optimum amount of diatomaceous earth to use when purifying viral vectors. It was found that using a high amount of diatomaceous earth actually caused a decrease in percentage recovery of viral vector. Without being bound by theory, this is thought to be because some of the viral vectors were lost by binding to the diatomaceous earth. Reducing the amount of diatomaceous earth has the added advantage of reducing the cost of goods when purifying viral vectors.

Therefore, in one embodiment, the amount of diatomaceous earth used to filter the cell culture is about 2 to about 4 g DE/litre/% of wet cell weight in the cell culture, such as between 2.5-3.5 g DE/litre/% of wet cell weight in the cell culture. In a further embodiment, the amount of diatomaceous earth used to filter the cell culture is about 3 g DE/litre/% of wet cell weight in the cell culture. In a yet further embodiment, the amount of diatomaceous earth used to filter the cell culture is 3.15 g DE/litre/% of wet cell weight in the cell culture.

It will be understood that references to "g DE/litre/% of wet cell weight" refer to the amount of DE to use (in grams) per litre (of culture) per percentage of wet cell weight. This can also be referred to as "x g/L of DE per % of wet cell weight" or "(g/L DE)/% wet cell weight". The ratio is calculated this way to ensure that the amount of DE added is related to the amount of biomass to remove, thus scaling the size of the filter to the amount of biomass to remove. For example, a culture with a 2% wet cell weight using DE at 3.5 g DE/litre/% of wet cell weight would require a total of 7 g of DE for each litre of culture.

In one embodiment, the method additionally comprises one or more further filtration steps. In a further embodiment, the further filtration step comprises a 0.45 µm filter. Such filters are commercially available, for example the SartoScale disposable (SARTOBRAN P 0.45 µm) filter capsule available from SARTORIUS AG.

The virus-producing cells described herein may be stably or transiently transfected. If the cells are transiently transfected, viral vectors are produced by transient co-transfection of viral genes into a host cell line. The viral genes may be introduced using bacterial plasmids which exist in the host cell for only a limited period of time because the viral genes remain on the plasmids and are not integrated into the host cell genome. As such, transiently transfected genetic material is not passed on to subsequent generations during cell division. If the cells are stably transfected, viral vectors are produced by viral genes which are integrated into the genome of the host cell line. As such, stably transfected genetic material is passed on to subsequent generations during cell division.

The present invention is used as an initial filtration step to remove cells and collect the supernatant which contains viral vectors which have budded from the cells (i.e. the virus producer cells). Therefore, the present invention may be used in the production of viral vectors which are secreted by the host cell, such as lentiviral vectors.

In one embodiment, the viral vector is a retroviral vector. Retroviruses are a family of viruses which contain a pseudo-diploid single-stranded RNA genome. They encode a reverse transcriptase which produces DNA from the RNA genome which can then be inserted into the host cell DNA. The method described herein may be used to produce retroviral vector particles, in particular replication defective retroviral vector particles. The retroviral vector particle may be selected from or derived from any suitable retrovirus.

In one embodiment, the retroviral vector is derived from, or selected from, a lentivirus, alpha-retrovirus, gamma-retrovirus or foamy-retrovirus, such as a lentivirus or gamma-retrovirus, in particular a lentivirus. Lentiviruses are able to infect non-dividing (i.e. quiescent) cells which makes them attractive viral vectors for gene therapy. Therefore, in a further embodiment, the retroviral vector is a lentiviral vector. In a further embodiment, the lentiviral vector is selected from the group consisting of HIV-1, HIV-2, SIV, FIV, EIAV and Visna. In a yet further embodiment, the lentiviral vector is HIV-1 or is derived from HIV-1. The genomic structure of many retroviruses may be found in the art. For example, details on HIV-1 may be found from the NCBI Genbank (Genome Accession No. AF033819). HIV-1 is one of the best understood retroviruses and is therefore often used as a viral vector.

In an alternative embodiment, the viral vector is an adeno-associated viral vector (AAV). AAV belong to the Parvoviridae family and are encoded by a single-stranded DNA genome. AAV are also frequently used as gene therapy vectors because they infect both dividing and quiescent cells. Another advantage of using these viral vectors in gene therapy is their lack of pathogenicity. Several serotypes have been described so far, therefore in one embodiment the adeno-associated viral vector is selected from: AAV1, AAV2, AAV3, AAV4, AAV5, AAV6, AAV7, AAV8, AAV9, AAV10, AAV11, AAV12 and AAV13. In a further embodiment, the adeno-associated viral vector is selected from: AAV8 or AAV9.

It will be understood that the viral vectors of the present invention may be used in methods of gene therapy. Therefore, in one embodiment, the viral vector additionally comprises one or more transgenes. This transgene may be a therapeutically active gene which encodes a gene product which may be used to treat or ameliorate a target disease.

The transgene may encode, for example, an antisense RNA, a ribozyme, a protein, a toxin, an antigen (which may be used to induce antibodies or helper T-cells or cytotoxic T-cells), an antibody or fragment thereof (such as a monoclonal antibody, single chain antibody, domain antibody or scFv), a T cell receptor or chimeric antigen receptor.

In one embodiment, the viral vector comprises multiple copies of the transgene, such as two or more, in particular three or more, copies of the transgene. In some cases more than one gene product is required to treat a disease, therefore in a further embodiment, the viral vector additionally comprises two or more, such as three or more, or four or more, different transgenes.

The aim of gene therapy is to modify the genetic material of living cells for therapeutic purposes, and it involves the insertion of a functional gene into a cell to achieve a therapeutic effect. Therefore, the viral vectors can be used to transfect target cells and induce the expression of the gene of potential therapeutic interest. The viral vector can therefore be used for treatment of a mammalian subject, such as a human subject, suffering from a condition including but not limited to, inherited disorders, cancer, and certain viral infections.

In one embodiment, the cell culture comprises mammalian cells. In a further embodiment, the mammalian cells are human or mouse cells. In a yet further embodiment, the cell culture comprises human cells. The transducing methods may be performed by methods well known in the art.

In one embodiment, the mammalian cells are selected from HEK cells (such as a HEK 293 cells or HEK 6E cells), CHO cells, Jurkat cells, KS62 cells, PerC6 cells, HeLa cells or a derivative or functional equivalent thereof. In a further embodiment, the mammalian cells are HEK 293 cells, or derived from HEK 293 cells. Such cells could be adherent cell lines (i.e. they grow in a single layer attached to a surface) or suspension adapted/non-adherent cell lines (i.e. they grow in suspension in a culture medium). In a yet further embodiment, the HEK 293 cells are HEK 293T cells. The term "HEK 293 cell" refers to the Human Embryonic Kidney 293 cell line which is commonly used in biotechnology. In particular, HEK 293T cells are commonly used for the production of various retroviral vectors. Other examples of suitable commercially available cell lines include T-REX (LIFE TECHNOLOGIES) cell lines.

It will be understood by the skilled person that the conditions used for the cell culture will be dependent upon the host cell used. Typical conditions, for example the culture medium or temperature to be used, are well known in the art. In one embodiment, culturing is performed by incubating the host cells under humidified conditions. In a further embodiment, the humidified conditions comprise incubating the transfected cells at 37° C. at 5% $CO_2$. In one embodiment, culturing is performed using a culture medium selected from: Dulbecco's modified Eagle's medium (DMEM) containing 10% (vol/vol) fetal bovine serum (FBS), DMEM containing hexadimethrine bromide (Polybrene), serum-free ULTRACULTURE medium (LONZA, Cat. No. 12-725F), or FREESTYLE Expression medium (THERMO FISHER, Cat. No. 12338-018). In one embodiment, the cell culture is fed during culturing, e.g. fed using Tryptone.

In one embodiment, the method is performed under physiological conditions, i.e. conditions that occur in nature. This helps maintain the stability and infectivity of the viral vector. Physiological conditions typically comprise a temperature range of 20-40° C., atmospheric pressure of 1 and pH of 6-8.

In one embodiment, the physiological conditions comprise a pH of about 6 to about 8, such as a pH of 6.5 to 8, in particular a pH of 6.8 to 7.5. In a yet further embodiment, the physiological conditions comprise a pH of about 7.

In one embodiment, the physiological conditions comprise a salt concentration of about 100 mM to about 500 mM, such as about 150 mM to about 350 mM. In one embodiment, the salt is selected from sodium chloride or magnesium chloride.

In one embodiment, the culturing is performed for at least 24 hours, such as at least 36 hours, 48 hours or 72 hours.

Once isolated, the viral vector particles may be concentrated for in vivo applications. Concentration methods include, for example, ultracentrifugation, precipitation or anion exchange chromatography. Ultracentrifugation is useful as a rapid method for viral vector concentration at a small scale. Alternatively, anion exchange chromatography (for example using Mustang Q anion exchange membrane cartridges) or precipitation (for example using PEG 6000) are particularly useful for processing large volumes of viral vector supernatants.

According to a further aspect of the invention, there is provided a viral vector particle obtained by the methods as defined herein.

The invention will now be described in further detail with reference to the following, non-limiting Examples.

EXAMPLES

Example 1: Optimisation of Dynamic Body Filtration to Maximise the Recovery of Lentivirus Cell Culture SARTORIUS BIOSTAT 2 L fermenters were used to grow HEK293 cells in FREESTYLE 293 media. PEI transfection of a 4 plasmid system was used to express the lentivirus. The cells were fed (Tryptone) 24 hours post infection and were harvested 48 hours post transfection.

Wet Cell Weight

Wet cell weights were determined by taking 10 ml samples into pre weighed 15 ml centrifuge tubes and centrifuging for 10 mins at 1000 g at 4° C. The supernatant was recovered into another pre weighed 15 ml centrifuge tube and the weights of both the pellet and the supernatant determined. These were used to calculate the wet cell weights, which are expressed in grams per litre and as a percentage.

| | | |
|---|---|---|
| Fermenter 7 | 21.98 g/L | (2.20%) |
| Fermenter 8 | 13.55 g/L | (1.35%) |

Dynamic Body Filtration (DBF1)

500 ml of culture was removed from Fermenter 8 and 5 g of diatomaceous earth {DE} added; this was mixed at room temperature for 30 mins [10 g/L is the maximum recommended amount of DE to use]. The sample was then filtered at 8 ml/min using a SARTORIUS custom DBF device with filter paper to capture the DE. In under an hour, 410 ml of material was filtered.

The filter was then flushed with 55 ml of PBS. Samples were taken and DBF1 filtered material was filtered using a SartoScale disposable (SARTOBRAN P 0.45 μm) filter capsule at 12 ml/min (pre wet with PBS for 10 mins).

Dynamic Body Filtration (DBF2)

9 g of diatomaceous earth was suspended in 100 ml of PBS and added directly to 1.2 L of culture in Fermenter 7.

This was mixed for 30 mins using the impeller at 100 rpm and mixture was then filtered at 12 ml/min using a SARTORIUS custom DBF device with filter paper to capture the dynamic body filter. In 45 mins, 515 ml of material was filtered.

The dynamic body filter was then flushed with 50 ml of PBS. Samples were taken and DBF2 filtered material was filtered using a SartoScale disposable (SARTOBRAN P 0.45 μm) filter capsule at 12 ml/min (pre wet with PBS for 10 mins).

Post Bioreactor Harvest Filter PB1 (SARTORIUS)

A SARTOCLEAR PB1 Filter Capsule (11 μm & 4 μm Pre Filter) was pre wetted using water for 15 mins and PBS for 10 mins at 6 ml/min. Sample from Fermenter 7 was then fed directly to the filter, which managed to process a total of 499 ml over approximately 80 mins.

The filter was then flushed with 50 ml of PBS. Samples were taken and PB1 filtered material was filtered using a SartoScale disposable (SARTOBRAN P 0.45 μm) filter capsule at 12 ml/min (pre wet with PBS for 10 mins).

Direct 0.45 μm Filtration

A SartoScale disposable (SARTOBRAN P 0.45 μm) filter capsule was pre wetted using water for 15 mins and PBS for 10 mins at 6 ml/min. Sample from Fermenter 7 was then fed directly to the filter, which managed to process a total of 65 ml prior to blocking.

Results

Filtrates were measured using p24 ELISA assay (CLONTECH) and Infectious Titer assay to determine the percentage recovery of lentiviral vector. Infectious Titer assays are well known in the art, for example see Geraerts et al. (2006) *BMC Biotechnology*, 6:34. The results are shown in Table 1, below.

TABLE 1

Results of p24 ELISA data and Infectious Titer Assay Data

| | % Recovery | First Stage | 0.45 μm | Total |
|---|---|---|---|---|
| DBF1 | TU | 57.3 | 73.9 | 40.2 |
| | p24 | 56.6 | 180.4 | 91.9 |
| DBF2 | TU | 89 | 96.1 | 74.5 |
| | p24 | 126.3 | 149.1 | 156.7 |
| PB1 | TU | 67.6 | 70.7 | 55.9 |
| | p24 | 132 | 81.5 | 95.8 |
| 0.45 μm | TU | | | 61.1 |
| | p24 | | | 84.8 |

Conclusions

Dynamic Body Filtration gives higher recoveries of infectious titer and p24 than either direct 0.45 μm filtration or filtration using a specific SARTORIUS harvesting filter PB1 (Post Bioreactor).

These data confirm our initial findings that dynamic body filtration, using diatomaceous earth, can be used successfully to harvest lentiviral supernatants directly from bioreactors with good recoveries of infectious titre and p24.

If an excess of diatomaceous earth is added prior to dynamic body filtration then there is a reduction in the recovery of infectious titer and p24. In experiment DBF1, 7.353 g DE/litre/% of wet cell weight was used and this gave 57.3% recovery of infections titer compared to experiment DBF2 which used 3.145 353 g DE/litre/% of wet cell weight which gave an 89% recovery of infectious titer.

The amount of diatomaceous earth used per percentage of wet cell weight looks to be an important variable that can be optimised when using dynamic body filtration. The data presented herein indicates that minimising the amount of diatomaceous earth used can actually maximise the recovery of lentivirus using dynamic body filtration.

It will be understood that the embodiments described herein may be applied to all aspects of the invention. Furthermore, all publications, including but not limited to patents and patent applications, cited in this specification are herein incorporated by reference as though fully set forth.

The invention claimed is:

1. A method of purifying a supernatant containing viral vectors from a cell culture, the method comprising: removing cells by filtering said cell culture using an amount of diatomaceous earth ranging from about 2 grams Diatomaceous earth (DE)/liter/% of wet cell weight to about 4 grams DE/litre/% of wet cell weight in the cell culture, wherein the cells are not lysed prior to filtering the cell culture and wherein the pH ranges from about 6 to about 8.

2. The method of claim 1, wherein the diatomaceous earth is added directly to a bioreactor containing the cell culture.

3. The method of claim 1, which additionally comprises one or more further filtration steps.

4. The method of claim 3, wherein the further filtration step comprises a 0.4 μm filter capsule.

5. The method of claim 1, wherein the amount of diatomaceous earth used is about 3 g DE/litre/% of wet cell weight in the cell culture.

6. The method of claim 1, wherein the viral vector is a retro viral vector or an adeno-associated viral vector (AAV).

7. The method of claim 6, wherein the retroviral vector is a lentiviral vector.

8. The method of claim 1, wherein the cell culture comprises HEK293 cells.

9. The method of claim 1, wherein the method is performed at a salt concentration of about 100 mM to about 350 mM.

10. The method of claim 9, wherein the salt is selected from the group consisting of sodium chloride and magnesium chloride.

11. A method of purifying a supernatant containing viral vectors from a cell culture, the method comprising the steps of:
   (i) calculating the percentage of wet cell weight in the cell culture;
   (ii) calculating the amount of diatomaceous earth to use when purifying the supernatant containing viral vectors from the cell culture so that the amount of diatomaceous earth is 2-4 g DE/litre/% of wet cell weight; and
   (iii) removing cells by filtering said cell culture using the amount of diatomaceous earth calculated in step (ii), wherein the cells are not lysed prior to filtering the cell culture and wherein the pH ranges from about 6 to about 8.

12. The method of claim 11, wherein the method is performed at a salt concentration of about 100 mM to about 350 mM.

13. The method of claim 12, wherein the salt is selected from the group consisting of sodium chloride and magnesium chloride.

* * * * *

UNITED STATES PATENT AND TRADEMARK OFFICE
CERTIFICATE OF CORRECTION

PATENT NO. : 11,021,700 B2
APPLICATION NO. : 15/677175
DATED : June 1, 2021
INVENTOR(S) : Paul Stephen Carter et al.

Page 1 of 1

It is certified that error appears in the above-identified patent and that said Letters Patent is hereby corrected as shown below:

On the Title Page

Item (72), add:
John Emerson, El Cajon, CA (US) Mihal Szelwicki, Essex, UK

Signed and Sealed this
Thirteenth Day of September, 2022

Katherine Kelly Vidal
*Director of the United States Patent and Trademark Office*